United States Patent [19]

Zuckerman

[11] Patent Number: 5,368,551
[45] Date of Patent: Nov. 29, 1994

[54] ANKLE BRACE WALKER

[75] Inventor: Raymond S. Zuckerman, Scottsdale, Ariz.

[73] Assignee: Saranda Corporation, Phoenix, Ariz.

[21] Appl. No.: 978,919

[22] Filed: Nov. 19, 1992

[51] Int. Cl.$^5$ .............................................. A61F 5/00
[52] U.S. Cl. ........................................ 602/23; 602/27
[58] Field of Search ................... 602/23, 27, 62, 60; 128/882, 869

[56] References Cited

U.S. PATENT DOCUMENTS

| 4,517,968 | 5/1985 | Greene et al. | 128/80 H |
|---|---|---|---|
| 4,572,169 | 2/1986 | Mauldin | 602/27 |
| 4,771,768 | 9/1988 | Crispin | 602/27 |
| 4,934,355 | 6/1990 | Porcelli | 128/80 H |
| 4,955,149 | 9/1990 | Ottieri | 36/119 |
| 4,962,760 | 10/1990 | Jones | 128/80 F |
| 4,974,583 | 12/1990 | Freitas | 602/27 |
| 5,031,607 | 7/1991 | Peters | 128/80 H |
| 5,078,128 | 1/1992 | Grim | 602/23 |
| 5,094,232 | 3/1992 | Harris | 602/27 |
| 5,176,623 | 1/1993 | Stetman | 602/27 |
| 5,183,036 | 2/1993 | Spademan | 602/27 |

Primary Examiner—Michael A. Brown
Attorney, Agent, or Firm—Cahill, Sutton & Thomas

[57] ABSTRACT

A pair of struts are frictionally and mechanically disengageably engaged with corresponding ones of opposed uprights of the base of an ankle brace walker to provide rigidity to an enveloped foot and ankle. The base includes a plurality of longitudinally aligned laterally offset flanges intermediate laterally aligned flanges, all of which flanges are disposed intermediate the sole and the foot bed of the base to provide rigidity for the foot and with sufficient strength to permit walking without danger of breakage of the base with resulting injury to a user. Cushioning means and strap means retain the foot and ankle comfortably but firmly within the ankle brace walker.

18 Claims, 3 Drawing Sheets

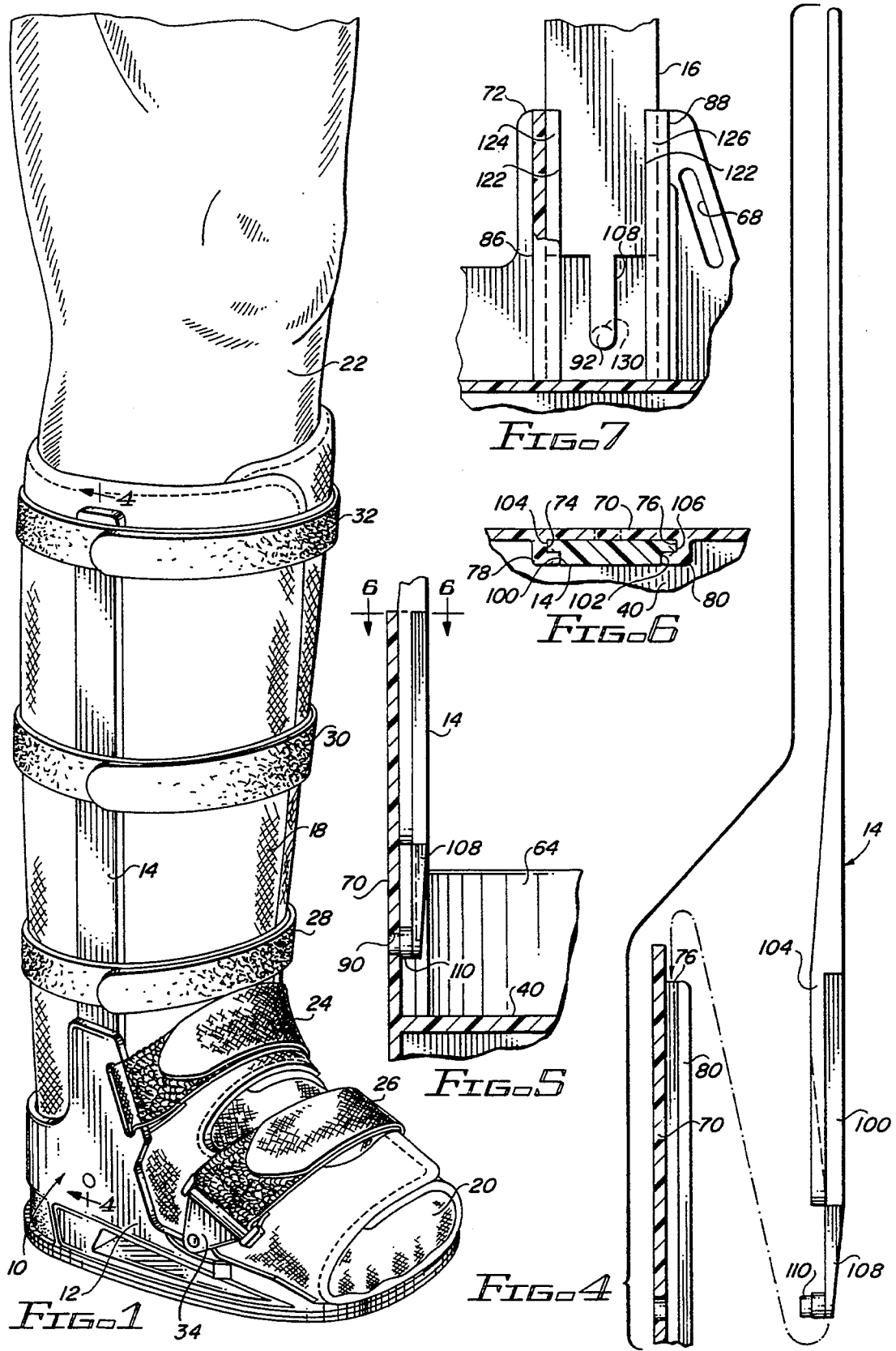

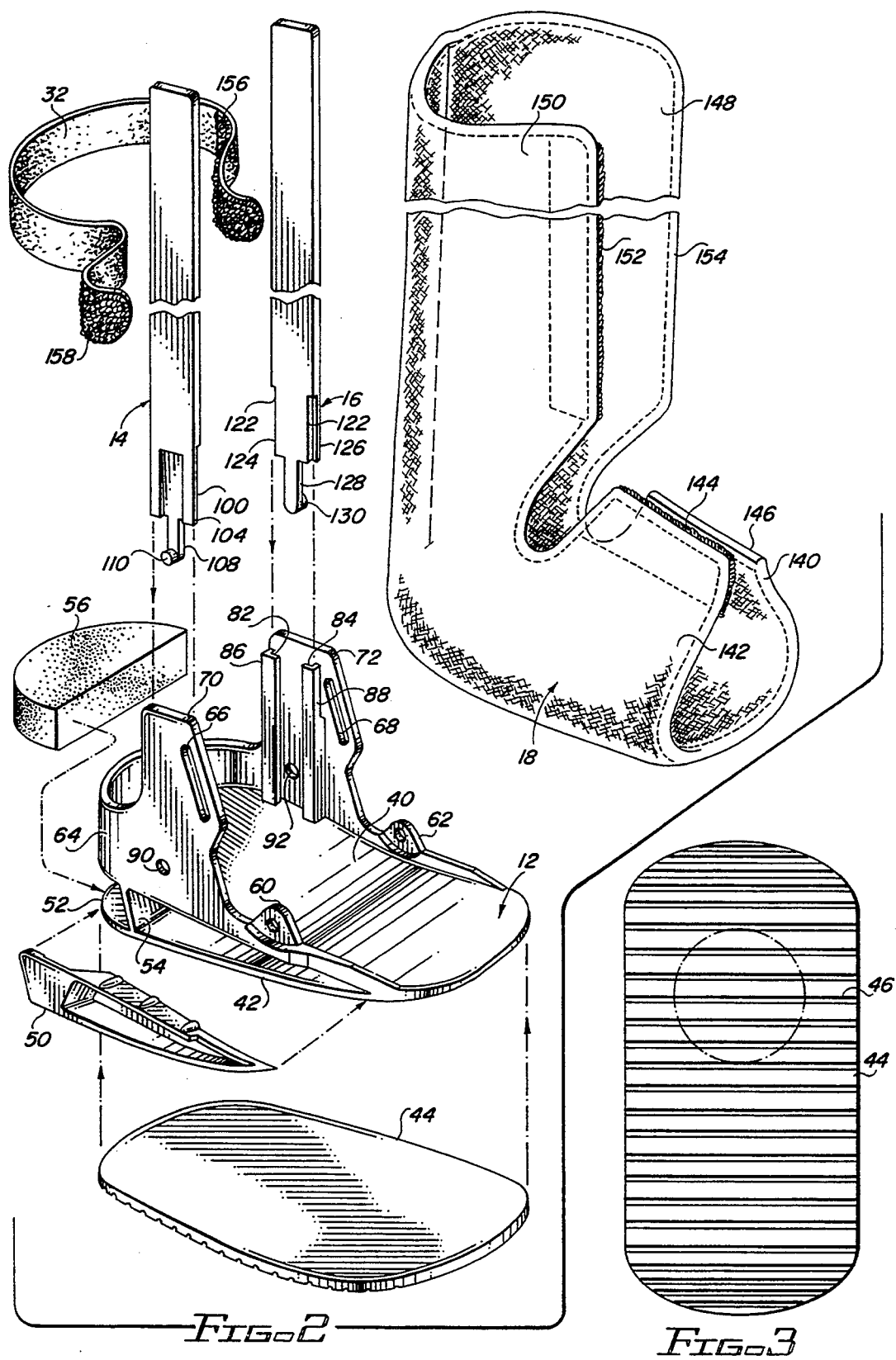

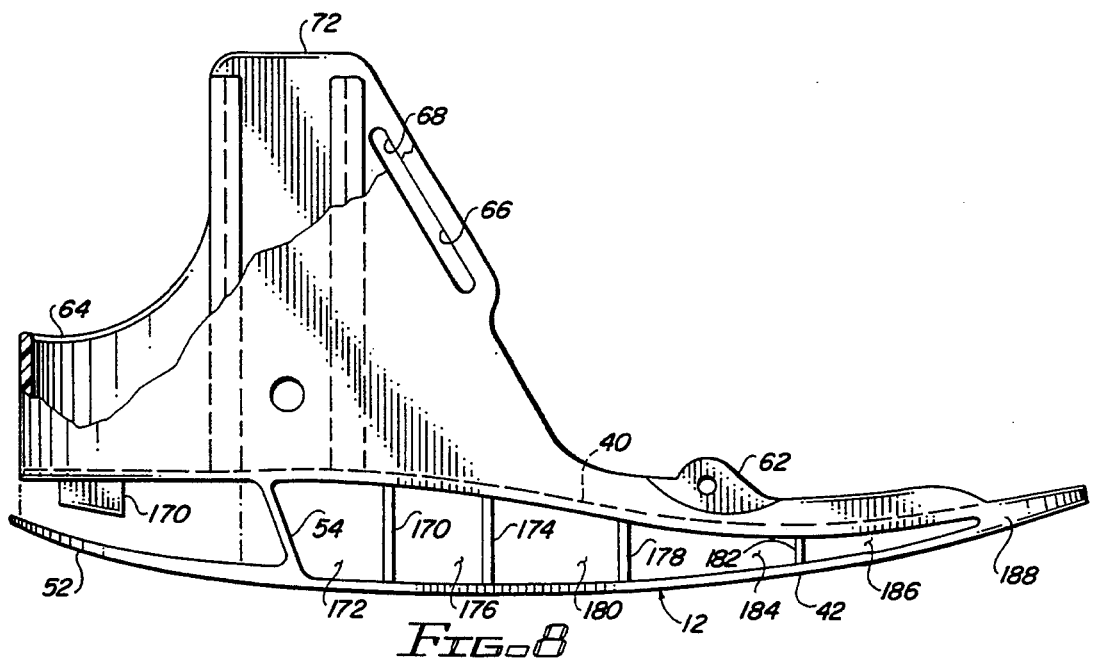
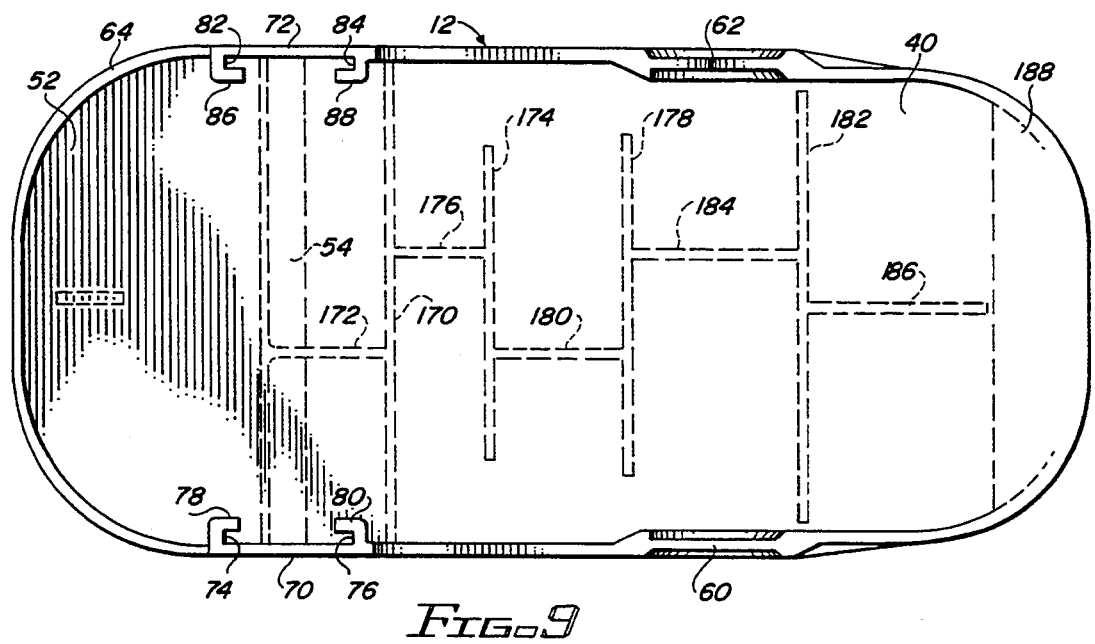

ANKLE BRACE WALKER

BACKGROUND OF THE INVENTION

1. Field of the Invention

The present invention relates to walkers and, more particularly, to ankle brace walkers having frictionally and mechanically detachably attached struts extending from a lightweight structurally rigid base.

2. Description of Related Art

For years, an injured or broken ankle or foot was encased a heavy plaster cast. Early medical opinions dictated that the injured person not walk on the cast. With further understanding of the healing and recuperative processes, plaster casts were made with load bearing inserts to permit walking. Such casts were inordinately heavy and tended to cause fatigue and strain of the affected leg muscles. Moreover, they were of great discomfort to the user.

With the developments in plastics and in molding techniques, various walkers were developed as intended substitutes for the plaster casts under certain circumstances. These walkers of plastic materials were more or less successful, depending upon the structural configuration and the mechanisms employed for retaining them in place. One of their major advantages over plaster casts was that of permitting a user to remove them at bedtime and during other periods of rest, assuming that sufficient healing had occurred to eliminate a likelihood of misalignment of knitting bones or damage to soft tissues.

Earlier and presently existing embodiments of walkers made of plastic materials suffer from one severe fault. The simple process of walking does in fact place significant stresses upon an ankle brace walker. As a consequence, many presently existing embodiments of ankle brace walkers tend to break unless a user walks very carefully and very gently.

Presently existing ankle brace walkers generally include a base having a foot bed for supporting the foot and a pair of struts extending upwardly from the base for supporting the ankle and lower leg. A removable foot and ankle encasing boot of soft material is used as an interface between the foot and lower leg and the ankle brace walker. Straps, extending from the base, secure the foot in place and further straps wrapped about the braces and the lower leg maintain the lower leg lodged between the struts.

In presently existing embodiments of ankle brace walkers, the junction between the struts and the boot are a weak point and breakage at the junction often occurs. Furthermore, the loads placed upon the base can be significant and the base may crack or split. Such breakage would exacerbate existing injuries and may be responsible for further injuries.

SUMMARY OF THE INVENTION

Each strut of a pair of struts are frictionally and mechanically detachably attached to corresponding opposed sides extending upwardly from the base of an ankle brace walker. The resulting junction locks the two elements with one another to synergistically increase the strength of the junction. The base includes a plurality of longitudinally aligned laterally offset flanges disposed intermediate laterally aligned flanges disposed intermediate the sole and foot bed of the base to avoid an aligned concentration of stresses.

It is therefore a primary object of the present invention to provide a rigid and robust ankle brace walker.

Another object of the present invention is to provide a high strength light weight ankle brace walker.

Yet another object of the present invention is to provide a frictional and mechanical interconnection between each strut of a pair of struts and the base of an ankle brace walker.

Still another object of the present invention is to provide a light weight high strength base for an ankle brace walker.

A further objection of the present invention is to provide a disengageably engaged junctions between a pair of struts and a base of an ankle brace walker.

A yet further objection of the present invention is to provide a synergistic junction between each strut of a pair of struts and a base of an ankle brace walker.

A still further object of the present invention is to provide a high strength light weight ankle brace walker of plastic material.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 illustrates a lower leg and foot encased within an ankle brace walker;

FIG. 2 is an exploded isometric view of the components of the ankle brace walker;

FIG. 3 is a bottom view of a tread attached to the sole;

FIG. 4 is an exploded view illustrating attachment of a strut taken along lines 4—4, as shown in FIG. 2;

FIG. 5 is a partial cross-sectional view illustrating the junction between a strut and the base;

FIG. 6 is a partial cross-sectional view taken along lines 6—6, as shown in FIG. 5;

FIG. 7 is a partial side view illustrating the junction between a strut and the base;

FIG. 8 is a partial side view of the base; and

FIG. 9 is a top view illustrating in phantom lines the interior construction of a base.

DESCRIPTION OF THE PREFERRED EMBODIMENT

Referring to FIG. 1, there is illustrated an ankle brace walker 10 of relatively lightweight plastic material. It includes a base 12 and a pair of upwardly extending struts 14 and 16 (of which only strut 14 is shown). A boot 18 of soft sheet-like material envelops the foot 20 and lower leg 22 of a user to shield the soft tissues against chaffing or abrasion at the points of contact with the ankle brace walker. A pair of straps 24 and 26 extend from anchor points (60 and 62, see FIG. 2) of base 12 and about the user's foot 20 to secure the foot within the base. A plurality of further straps, such as straps 28, 30 and 32, are wrapped about struts 14 and 16 the retain lower leg 22 within and supported by the struts. Infinite adjustment of the straps may be achieved by using a hook and loop type fastening means to secure each of the straps. Furthermore, if boot 18 is of fibrous material, the hook type fastening means of the straps will engage and retain the boot in place to further stabilize a user's foot and lower leg within the ankle brace walker. It is to be understood that the number of straps and the method of wrapping the straps may be different from that illustrated.

Referring jointly to FIG. 2, 4, 5, 6 and 7, further details attendant base 10, struts 14 and 16 and boot 18 will be described. Base 12 includes a foot bed 40 for supporting a user's foot and a sole 42 for supporting the base upon the ground. As illustrated in FIG. 3, the sole may include a tread or an overlay 44 of rubber-like material to prevent slipping or skidding of the ankle brace walker across the floor or ground walked upon. The overlay may include a plurality of laterally aligned grooves 46 serving in the manner of a tread. Opposed side walls, of which side wall 50 is illustrated, close the space between foot bed 40 and sole 42. A curved heel segment 52, formed as part of sole 42, extends rearwardly from slanted flange member 54. The heel segment is cantilevered rearwardly of the flange member to provide a cushioning effect during the act of walking. An insert 56 of resilient foam-like material is inserted between heel segment 52 and the corresponding heel segment of foot bed 40 to provide a cushioning effect.

A pair of anchor members 60 and 62 extend upwardly from opposed sides at the forward portion of foot bed 40 for anchoring strap 26 in place (as illustrated in FIG. 1). A rear side wall 64 extends upwardly from the perimeter of the center and rear portion of foot bed 40 to position and stabilize the heel and ankle of a user. Slots 66 and 68 formed in wall 64 serve as anchor points for attaching and securing strap 24 (see FIG. 1). Wall 64 also includes upright members 70 and 72 for supporting struts 14 and 16, respectively. These uprights are essentially mirror images of one another and the description of one upright will be applicable to the description of the other upright.

Upright 70 includes a pair of opposed slots 74 and 76 formed on the inside of the upright by right angle flanges 78, 80 extending upwardly along the upright. Similarly, upright 72 includes a pair of opposing slots 82 and 84 formed by a pair of right angle flanges 86 and 88 formed on the interior surface of the upright. An opening 90 is formed intermediate slots 74, 76 in upright 70. A similar opening 92 is formed intermediate slots 82, 84 of upright 72. Both of these openings are disposed proximate the lower end of the respective uprights.

Strut 14 is in the manner of an upwardly extending strap to provide some flexibility but yet sufficient rigidity to retain an encased upper leg 22 of a user in relatively stable relationship with the user's foot 20. The lower end of the strut includes longitudinally extending indentations 100, 102 to define lips 104, 106, respectively. Lips 104, 106 are of a width and depth corresponding with respective slots 74, 76 to provide a sliding frictional fit therebetween to minimize relative movement between strut 14 and upright 70. For additional rigidity, the fit between lips 104, 106 and slots 74, 76 may be an interference fit. A tang 108 extends from the lower end of strut 14 and includes a button 110 disposed at the lower end of the tang. The button is sized to penetrably engage opening 90 in upright 70. The purpose of tang 108 is that of providing a cantilevered support for button 110 to retain the button within opening 90. Thereby, the engagement of the button with the opening provides a mechanical lock to preclude withdrawal of upright 14 under normal use. Yet, strut 14 may be disengaged from upright 70 by bending tang 108 to disengage button 110 from opening 90 and thereafter the strut may be drawn upwardly out of engagement with opposing slots 74, 76. Strut 16 is duplicative with strut 14 and includes a pair of indentations 120, 122 defining lips 124, 126, which lips engage slots 82, 84, respectively. A tang 128 extends downwardly from strut 16 to support a button 130. The button penetrably engages opening 92 in upright 72. Because of the frictional fit between each strut and its respective upright, the strength of the resulting junction is greater than the sum of the strengths of the two parts. Thus, a synergistically strengthened junction is achieved.

Boot 18 may be of sheet material, as described above or it may be generally molded, as depicted in FIG. 2. The boot includes overlapping flaps 140, 142 for wrapping the foot part of the boot about a user's foot. The flaps may be secured adjacent one another by hook and loop fastening means 144, 146. The boot may include the further pair of flaps 148, 150 for wrapping the upper part of the boot about lower leg 22 of a user. These flaps may be secured adjacent one another by hook and loop fastening means 152, 154. Strap 32, shown in FIG. 2, is representatively illustrated and may include hook fastening means 156 for engaging loop fastening means 158 to permit infinite adjustment and readjustment of the strap.

Referring primarily to FIGS. 8 and 9, details attendant base 12 will be described. A tab 170 extends downwardly from foot bed 40 into penetrable engagement with insert 56 (see FIG. 2) to retain the insert in place between the foot bed and heel segment 52. Flange member 54 extends laterally across base 12 to provide vertical support between the foot bed and the sole. A vertically aligned flange 170 extends across the base for vertical support and is stabilized by longitudinally extending vertical flange 172 interconnecting flange 170 with flange 54. A flange 174 extends vertically between the foot bed and the sole but terminates laterally short of the opposed sides of the base. A longitudinally aligned flange 176 interconnects flange 170 with flange 174. It may be noted that flange 176 is laterally offset from flange 172. A flange 178 extends vertically between foot bed 40 and sole 42 but terminates short of the opposed lateral sides of base 12. It may be noted that flanges 174 and 176, being short of the edge of the base, accommodate closure means, such as side wall 50. A longitudinally extending flange 180 interconnects flange 174 with flange 178. It may be noted that flange 180 is laterally offset from flange 176 and may be longitudinally aligned with flange 172, as illustrated. A yet further flange 182 vertically interconnects the foot bed with the sole and extends laterally essentially to opposed sides of the base. A longitudinally aligned flange 184 interconnects flange 178 with flange 182. It may be noted that flange 184 is laterally offset from flange 180 and may be aligned with flange 176, as illustrated. A further longitudinally aligned flange 186 extends forwardly from the approximate midpoint of flange 182 to provide vertical support between foot bed 40 and sole 2. This flange may be non aligned with flanges 172, 176, 180 and 184, as illustrated. Flange 186 extends forwardly to the solid junction 188 between foot bed 40 and sole 42. The open sides between foot bed 40 and sole 42, as illustrated in FIG. 2, are closed by a pair of dimensionally conforming side walls, such as side wall 50 illustrated in FIG. 2. These side walls provide vertical spacing and support between the corresponding lateral edges of the foot bed and the sole. These side walls may be secured in place by conventional techniques, such as heat welding, adhesives, etc. or by a snap fit mechanism.

Upon inspection, it will become apparent that the laterally offset longitudinally aligned flanges 172, 176, 180, 184 and 186 provide a discontinuous longitudinally aligned lines of stress during use of the ankle brace walker. Such discontinuities prevent concentration of stresses that might lead to failure or splitting of the base. Moreover, the egg crate-like construction intermediate the foot bed and the sole provides an extremely rigid base to prevent twisting or bending of the base that might be injurious to a user as well as being prone to failure. The only flexible segment of the base is at the heel for purposes of reducing jarring of a user's foot during walking. Flexibility at this location is unlikely to result in failure or loss of rigidity to the support provided to a user due to the robustness afforded by rear side wall 64 extending about the perimeter at the rear of the foot bed. Junction 188, being relatively thick, may bend during walking but is unlikely to split or fracture during normal use. Even if such damage were to occur, it would have no effect upon the rigid support provided by the remaining part of base 12.

While strap 26 (see FIG. 1) is shown as extending from anchor points 60, 62 by means of fittings, such as fitting 34, other attachment means may be employed and the location of the anchor points may be altered to suit particular medical or structural requirements. Furthermore, while strap 24 is shown as being in engagement with slots 66, 68 other attachment means may be used and the location may be altered for medical and/or structural reasons. While straps 28, 30 and 32 are depicted as being in the nature of three bands inscribing struts 14 and 16, boot 18 and the enveloped lower leg 22, a different arrangement, number and mode of wrapping of the straps may be employed for medical and/or structural reasons. Furthermore, the configuration and material of boot 18 may be varied to meet special medical requirements or for purposes of increasing the comfort of a user.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

I claim:

1. An ankle brace walker for supporting an injured foot and lower leg, said ankle brace comprising in combination:
   a) a unitary base having a longitudinal axis and a lateral axis and incorporating a foot bed for supporting the foot and a sole for supporting said walker upon a surface to be traversed, said base including:
      i) a plurality of laterally oriented flanges interconnecting said foot bed and said sole, and
      ii) a plurality of longitudinally oriented flanges interconnecting said foot bed and said sole with each single one of said plurality of longitudinally oriented flanges interconnecting adjacent ones of said laterally oriented flanges to define an egg crate like structure having open lateral sides;
   b) a pair of opposed side walls interconnecting opposed sides of said foot bed and said sole to close the open lateral sides of said base;
   c) a pair of uprights, one upright of said pair of uprights extending from each opposed side of said base, each upright of said pair of uprights including a pair of opposed slots and an opening;
   d) a first strut extending from one upright of said pair of uprights and a second strut extending upwardly from the other upright of said pair of uprights, each of said first and second struts including a pair of opposed lips for frictionally engaging said opposed slots in one upright of said uprights and a button for engaging said opening in the respective one of said pair of uprights to mechanically inhibit disengagement between said pair of opposed lips of said strut and said pair of opposed slots of said upright.

2. The ankle brace walker as set forth in claim 1 including a rear side wall extending from said base for interconnecting said pair of uprights.

3. The ankle brace walker as set forth in claim 1 wherein the fit between said pair of opposed lips of each of said first and second struts and said pair of opposed slots of the respective one of said uprights is an interference fit.

4. The ankle brace walker as set forth in claim 1 wherein each of said first and second struts includes a depending tang for supporting said button.

5. The ankle brace walker as set forth in claim 4 wherein each said tang comprises a flexible element for urging positioning of the respective one of said buttons within the respective one of said openings.

6. The ankle brace walker as set forth in claim 1 including a boot for enveloping a user's foot and lower leg.

7. The ankle brace walker as set forth in claim 6 including strap means for securing a user's boot enveloped foot and lower leg upon said base and intermediate said struts.

8. The ankle brace walker as set forth in claim 7 including means disposed on said base for securing said straps.

9. The ankle brace walker as set forth in claim 1 wherein each longitudinal flange of said plurality of longitudinally oriented flanges is laterally offset from and non aligned with an adjacent longitudinal flange of said plurality of longitudinal flanges.

10. The ankle brace walker as set forth in claim 1 wherein said plurality of longitudinally oriented flanges and said plurality of laterally oriented flanges are disposed in planes essentially perpendicular to said sole.

11. The ankle brace walker as set forth in claim 10 including a further laterally oriented flange disposed at an angle with respect to the planes of said longitudinally and laterally oriented flanges.

12. An ankle brace walker for supporting an injured foot and lower leg, said ankle brace walker comprising in combination:
   a) a base incorporating a foot bed for supporting the foot and a sole for supporting said walker upon a surface to be traversed, said base including an egg crate like structure interconnecting and formed as part of said foot bed and said sole and including open sides;
   b) a pair of opposed side walls secured to said base for closing the open sides of said egg crate structure;
   c) a pair of uprights, one upright of said pair of uprights extending from each opposed side of said base, each upright of said pair of uprights including a pair of opposed slots and an opening;
   d) a first strut extending upwardly from one upright of said pair of uprights and a second strut extending upwardly from the other upright of said pair of uprights, each of said first and second struts including a pair of opposed lips for frictionally engaging said opposed slots in one upright of said pair of uprights and a button for engaging said opening in the respective one of said pair of uprights to mechanically inhibit disengagement between said pair of opposed lips of said strut and said pair of opposed slots of said upright.

13. The ankle brace walker as set forth in claim 12 wherein the fit between said pair of opposed lips of each of said first and second struts and said pair of opposed slots of the respective one of said pair of uprights is an interference fit.

14. The ankle brace walker as set forth in claim 12 wherein each of said first and second struts includes a depending tang for supporting said button.

15. The ankle brace walker as set forth in claim 14 wherein each said tang comprises a flexible element for urging positioning of the respective one of said buttons within the respective one of said openings.

16. An ankle brace walker for supporting an injured foot and lower leg, said ankle brace walker comprising in combination:

a) a base incorporating a foot bed for supporting the foot and a sole for supporting said walker upon a surface to be traversed;
b) a pair of uprights, one upright of said pair of uprights extending from each opposed side of said base, each upright of said uprights including a pair of opposed slots and an opening;
c) a first strut extending upwardly from one upright of said pair of uprights and a second strut extending upwardly from the other upright of said pair of uprights, each of said first and second struts including a pair of opposed lips for frictionally engaging said opposed slots in the respective one of said pair of uprights and a button for engaging said opening in the respective one of said pair of uprights to mechanically inhibit disengagement between said pair of opposed lips of said strut and said pair of opposed slots of said upright.

17. The ankle brace walker as set forth in claim 16 wherein each of said first and second struts includes a depending tang for supporting said button.

18. The ankle brace walker as set forth in claim 17 wherein each said tang comprises a flexible element for urging positioning of the respective one of said buttons within the respective one of said openings.

* * * * *